(12) United States Patent
Bender et al.

(10) Patent No.: US 11,717,530 B2
(45) Date of Patent: Aug. 8, 2023

(54) BLOCKADE OF MIR4661-3P BINDING TO IL-17A MRNA WITH SITE-SPECIFIC TARGET SITE BLOCKER PREVENTS NEURO-INFLAMMATORY-MEDIATED DISEASE

(71) Applicant: YALE UNIVERSITY, New Haven, CT (US)

(72) Inventors: Jeffrey Bender, Orange, CT (US); Vinod Ramgolam, New Haven, CT (US); Timur Yarovinsky, Woodbridge, CT (US)

(73) Assignee: YALE UNIVERSITY, New Haven, CT (US)

( * ) Notice: Subject to any disclaimer, the term of this patent is extended or adjusted under 35 U.S.C. 154(b) by 5 days.

(21) Appl. No.: 17/052,916

(22) PCT Filed: May 7, 2019

(86) PCT No.: PCT/US2019/031098
§ 371 (c)(1),
(2) Date: Nov. 4, 2020

(87) PCT Pub. No.: WO2019/217407
PCT Pub. Date: Nov. 14, 2019

(65) Prior Publication Data
US 2021/0069233 A1    Mar. 11, 2021

Related U.S. Application Data

(60) Provisional application No. 62/667,763, filed on May 7, 2018.

(51) Int. Cl.
*C07H 21/04*     (2006.01)
*A61K 31/7125*  (2006.01)
*A61P 21/00*    (2006.01)
*C12N 15/113*   (2010.01)

(52) U.S. Cl.
CPC .......... *A61K 31/7125* (2013.01); *A61P 21/00* (2018.01); *C12N 15/113* (2013.01)

(58) Field of Classification Search
None
See application file for complete search history.

(56) References Cited

U.S. PATENT DOCUMENTS

| | | |
|---|---|---|
| 2007/0160576 A1 | 7/2007 | Arnott et al. |
| 2011/0289608 A1 | 11/2011 | Schnell et al. |
| 2011/0300154 A1 | 12/2011 | Umetsu et al. |

OTHER PUBLICATIONS

Shao, Yu, et al. "Rational design and rapid screening of antisense oligonucleotides for prokaryotic gene modulation." Nucleic acids research 34.19 (2006): 5660-5669.*
Chen, Kong, and Jay K. Kolls. "Interluekin-17a (il17a)." Gene 614 (2017): 8-14.*
International Search Report and Written Opinion issued by the International Searching Authority dated Sep. 20, 2019 for International Application No. PCT/US2019/031098, 11 pages.
Nolin, James D., et al., "The glutaredoxin/S-glutathionylation axis regulates interleukin 17A-induced pro-inflammatory responses in lung epithelial cells in association with S-glutathionylation of Nuclear Factor kappa B family proteins", Free Radical Biology Medical (0), Aug. 2014, pp. 143-153.

* cited by examiner

*Primary Examiner* — Kimberly Chong
(74) *Attorney, Agent, or Firm* — Saul Ewing LLP; Kathryn Doyle; Justin Crotty

(57) ABSTRACT

In various aspects and embodiments the invention provides compositions and methods useful in the treatment of inflammatory disease, in particular, multiple sclerosis.

6 Claims, 8 Drawing Sheets

Specification includes a Sequence Listing.

The non-conventional role of miR466l-3p in mRNA stablization

Conventional function of miRNA

Enhancing role of miR466l-3p

⊂⊃ Target site

Vehicle　　　　　　　TSB

SEQUENCE LISTING

```
<160> NUMBER OF SEQ ID NOS: 5

<210> SEQ ID NO 1
<211> LENGTH: 5452
<212> TYPE: DNA
<213> ORGANISM: homo sapien

<400> SEQUENCE: 1
aacagaaaat ctcgtgtctc ttgaacctag ttatttattc cttgagcaga gtagatattc      60
aacaaaagaa ttgttaaatt caattaaata ggatatatct tattattaaa tattttttc     120 atttttttgtt tacttatatg atgggaactt gagtagtttc cggaattgtc tccacaacac    180
ctggccaagg aatctgtgag gaaaagaaag atcaaatgga aaatcaaggt acatgacacc    240
agaagaccta catgttactt caaactttt cttcctcatg aaccattaaa atagagcata     300
actcttctgg cagctgtaca tatgttcata aatacatgat attgacccat agcatagcag    360
ctctgctcag cttctaacaa gtaagaatga aaagaggaca tggtctttag gaacatgaat    420
ttctgccctt cccatttttcc ttcagaagga gagattcttc tatgacctca ttgggggcgg    480
```

```
aaattttaac caaaatggtg tcacccctga acccactgcg acacgccacg taagtgacca    540
cagaaggaga aaagccctat aaaagagag acgatagcgc tacattttgt ccatctcata    600
gcaggcacaa actcatccat ccccagttga ttggaagaaa caacgatgac tcctgggaag    660
acctcattgg tggtgagtcc tgcactaacg tgcgatgctc ttgctgattt ggaccagata    720
gtatttctgg accgtgggca tgaaacgctg ggttctgact atggagatcc aggaatactg    780
tatatgtagg ataggaaatg aaagctttgg taggtattta agtcattgtg cagcattttc    840
aagaactgat acacagcagt ttgaaagata agattaaaac tgaaagatag ctatattggg    900
gctaaaccac acaagaagtg tcacatgatg ctgtgcagta agaaagaaaa tttattgaaa    960
gtctgttttt ctgagtacaa aggatttaat ataattctcc cacggcattt ttctttaaaa    1020
tgggtcacta tccttgagat tttgaaagcc gtagcagcaa caacctttgt ttccattatc    1080
tcgtaccata ttctcagtac attgaaacta tgtattctaa ctaaacatag gtataactgt    1140
gttttagaat aagtggggtt tatattttt aaatatttaa cttcaagtat cttttttgaa    1200
atctgatttt attacagaat caatacatgt taaatttaga acaactggaa aatataccta    1260
agaaaacatg aaggagatcg agttttagt tggatgcctg ccagtagcac caacagcact    1320
tctagcatga atattgatac cacatagatt ttctatagct cttcttcca atgtgaatgt    1380 ttgacttcac gatgagtttc acagaatatg ggactgagaa caatggtgca ggaggatatt    1440
tctacctaga aaatcaaggt tattattcct tcccagacct gacaatgatg catgtgctga    1500
taggctaatg acatgccatg acttgacatt tttattaaaa ttattgccaa ccaatggata    1560
acatgtcttt cctaagtcaa aaggagaatg ttgaaactag tttttttaaa aaaattttaa    1620
agccatggtg ttaacattat gttggtcatc tacctagatt tttctctagc tgatctgaaa    1680
aatgtagtat agattgtcct ggaacattgt gtgttctcta tgattagcaa tgcatcatca    1740
tcacaattaa tttgtcaaaa agaaccacat agtaatctaa tctccaacct ctctctcctt    1800
tcccattcaa ttctagtcac tgctactgct gctgagcctg gaggcatag tgaaggcagg    1860 aatcacaatc ccacgaaatc caggatgccc aaattctgag acaagaact tcccccggac    1920 tgtgatggtc aacctgaaca tccataaccg gaataccaat accaatccca aaaggtcctc    1980
agattactac aaccgatcca cctcaccttg gaatctccag tacgtaaagc ttccagataa    2040
aaatgctata ttcttcatcc ctcttatgca tcagactgcc agttaaatct ccctgaggat    2100
gattttattc atttagaatt accagtcaaa cctggaagga ccactgtgaa gagcaattct    2160
caaactttct acagatttct ttaaccaagc acaggacagc ctccaataat ccctatcctg    2220
ttagatctaa ttgtcactga caccaataat caacccaaat taattataat cattattcta    2280
atatttatga gaccccaagt ctattcttta tttattcaaa gaatagacat ttatcaaaga    2340
ggattaatgc ttttattatc ttaaccagag ctgccattga aagatttat tgcaaataat    2400 taataattag ggttttttac ttttattctt tgcttatttt ttgttttga atcccagtgg    2460 aataagtatc actggggtat tctaccccct ttgtgtgtta aatagtcttg atctacttcc    2520
taacatacct atgcttgctg tatccttagt atacccagta tttagacccc atcaagggtt    2580
aaataccaaa tgtattttga tcatttgact tcatacaaat aagtctctgt tctgtgggagc    2640 ctacagattg gtctgattgt aggatttctt ctcttcttcc cattactagg aagagtcaaa    2700
ataaatcaat tcaaaaatgc aagcaaatca ttcactgatc taaagagag agggaagaga    2760 aggtcataga gacacttaac cttttgtttc cagcccttta tctcagctct gggctctgtc    2820
```

```
ccacgaatgt gatctcagat aaaattttga tgtattccct cttcaaagac agacttcatc    2880
aagtcaaata aacagctatc ttattctaga tggttccaag tctactcttc ctttggtctt    2940
cttctgtctg tcaaatgtac cctaaaaaag ctatcatttg tgtcaaactt aaattttttc    3000
tgtggcctca gtctatctta ttttattcat tcttcaaata aattggagaa aaactgatca    3060
ctgtcttctt ttctataaca attcacgtgc ttgaaaaaaa aatccaattt gtccccaaag    3120
ttcttcttca aactaacatc atttaaagaa tttgcaatgc ctataatttg tcatcctgtg    3180
aacttgcctc tcttcatgta ttcctgtttt atttctttcc cactttacca ggaattcact    3240
ttcctcctga ttttttctccc ctctgcagcc gcaatgagga ccctgagaga tatccctctg    3300
tgatctggga ggcaaagtgc cgccacttgg gctgcatcaa cgctgatggg aacgtggact    3360
accacatgaa ctctgtcccc atccagcaag agatcctggt cctgcgcagg agcctccac     3420 actgccccaa ctccttccgg ctggagaaga tactggtgtc cgtgggctgc acctgtgtca    3480
ccccgattgt ccaccatgtg gcctaagagc tctgggagc ccacactccc caaagcagtt    3540
agactatgga gagccgaccc agcccctcag gaaccctcat ccttcaaaga cagcctcatt    3600
tcggactaaa ctcattagag ttcttaaggc agtttgtcca attaaagctt cagaggtaac    3660
acttggccaa gatatgagat ctgaattacc tttccctctt tccaagaagg aaggtttgac    3720
tgagtaccaa tttgcttctt gtttactttt ttaagggctt taagttattt atgtatttaa    3780
tatgccctga gataactttg gggtataaga ttccatttta atgaattacc tactttattt    3840
tgtttgtctt tttaaagaag ataagattct gggcttggga attttattat ttaaaaggta    3900
aaacctgtat ttatttgagc tatttaagga tctatttatg tttaagtatt tagaaaaagg    3960
tgaaaaagca ctattatcag ttctgcctag gtaaatgtaa gatagaatta aatggcagtg    4020
caaaatttct gagtctttac aacatacgga tatagtattt cctcctcttt gttttttaaaa   4080 gttataacat ggctgaaaag aaagattaaa cctactttca tatgtattaa tttaaatttt    4140
gcaatttgtt gaggttttac aagagataca gcaagtctaa ctctctgttc cattaaaccc    4200
ttataataaa atccttctgt aataataaag tttcaaaaga aaatgtttat ttgttctcat    4260
taaatgtatt ttagcaaact cagctcttcc ctattgggaa gagttatgca aattctccta    4320
taagcaaaac aaagcatgtc tttgagtaac aatgacctgg aaataccacaa aattccaagt   4380 tctcgatttc acatgccttc aagactgaac accgactaag gttttcatac tattagccaa    4440
tgctgtagac agaagcattt tgataggaat agagcaaata agataatggc cctgaggaat    4500
ggcatgtcat tattaaagat catatgggga aaatgaaacc ctccccaaaa tacaagaagt    4560
tctgggagga gacattgtct tcagactaca atgtccagtt tctcccctag actcaggctt    4620
cctttggaga ttaaggcccc tcagagatca acagaccaac attttctct tcctcaagca     4680 acactcctag ggcctggctt ctgtctgatc aaggcaccac acaacccaga aaggagctga    4740
tggggcagaa cgaactttaa gtatgagaaa agttcagccc aagtaaaata aaaactcaat    4800
cacattcaat tccagagtag tttcaagttt cacatcgtaa ccattttcgc ccccatggcc    4860
catgtgctgt cttgccctac ttctgaaggc ctctagatat tctcaggcca ctctgcaggc    4920
tccctgcttc ttgaaagacc ttcctcttca ctccatcctg ctccatccag tgtgctccag    4980
cccacccaga ggcccatggc ttttctaggc ttctttccct attccaaatc cagggggttgg   5040 cctctccagc cacctcctct cagtcatttt gtgctcacat cttgattcct gtgaccatcc    5100
ctgtcaccat tttcctacag gaaatcccca ggcagcttcc agggacagtt cctcacagcc    5160
tttacgcttt caagcttctc actaaaaacc tgctgctcgt tttcaagctt tctctgaacg    5220
```

```
gtgatgatga aagaaaaaa ttgtttttgt ttttgttggg agagggagtt gtaaaggatg    5280
tatatgtcta tatgtgtgtg tgtgtgtgtg tgtgtggtcc tgaaccatta tttcccacta    5340
gattttgggt gggggtatg cggatgggaa gaggcagttg ctttccatgt actcctcccc    5400
tgatacactt tgcttttatt ctctcttcat tttccccagt tagcactacc at           5452
```

<210> SEQ ID NO 2
<211> LENGTH: 27
<212> TYPE: RNA
<213> ORGANISM: Artificial Sequence
<220> FEATURE:
<223> OTHER INFORMATION: Target site blocker

<400> SEQUENCE: 2

```
ccuagauaaa uacaaauaca aauucaa                                         27
```

<210> SEQ ID NO 3
<211> LENGTH: 155
<212> TYPE: PRT
<213> ORGANISM: Homo sapiens

<400> SEQUENCE: 3

```
Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155
```

<210> SEQ ID NO 4
<211> LENGTH: 21
<212> TYPE: DNA
<213> ORGANISM: Artificial Sequence
<220> FEATURE:
<223> OTHER INFORMATION: target site blocker

<400> SEQUENCE: 4

```
acttaaacat aaatagatcc t                                               21
```

```
<210> SEQ ID NO 5
<211> LENGTH: 44
<212> TYPE: RNA
<213> ORGANISM: Homo sapiens

<400> SEQUENCE: 5
auuuauuuga gcuauuuaag gaucuauuua uguuuaagua uuua          44
```

BLOCKADE OF MIR4661-3P BINDING TO IL-17A MRNA WITH SITE-SPECIFIC TARGET SITE BLOCKER PREVENTS NEURO-INFLAMMATORY-MEDIATED DISEASE

CROSS REFERENCE TO RELATED APPLICATIONS

The present application is a 35 U.S.C. § 371 national phase application from, and claiming priority to, International Application No. PCT/US2019/031098, filed May 7, 2019, which claims priority under 35 U.S.C. § 119(e) to U.S. Provisional Patent Application No. 62/667,763 filed May 7, 2018, which are hereby incorporated by reference in their entireties herein.

STATEMENT REGARDING FEDERALLY SPONSORED RESEARCH OR DEVELOPMENT

This invention was made with government support under AI124116 awarded by the National Institutes of Health. The government has certain rights in the invention.

BACKGROUND OF THE INVENTION

IL-17A levels are increased in the central nervous systems (CNS) lesions of multiple sclerosis (MS) patients. Elevated IL-17 mRNA is increased in active MS brain lesions, compared to normal-appearing white matter. This is also observed at the IL-17A protein level. There are currently IL-17A neutralizing Abs in clinical trials for the treatment of MS, but results have been negative to date. There is a need for compositions and methods that could be used to reduce levels of IL-17A. The present disclosure addresses this need.

SUMMARY OF THE INVENTION

In one aspect the invention provides a composition comprising a polyribonucleic acid comprising the sequence ATAAATA and at least one modification selected from the group consisting of locked nucleic acid, bridged nucleic acid, phosphorothioate nucleic acid and peptide nucleic acid.

In various embodiments, the polyribonucleic acid is a locked nucleic acid with a phosphorothioate backbone.

In various embodiments, further comprising at least one pharmaceutically acceptable excipient.

In various embodiments, the polyribonucleic acid is encoded by a deoxyribonucleic acid comprising the sequence SEQ ID NO: 4 ACTTAAACATAAATAGATCCT.

In various embodiments, the invention provides a method of treating an IL-17A mediated disease in a subject in need thereof, comprising administering to the subject a therapeutically effective amount of a composition of the invention.

In various embodiments, the IL-17A mediated disease is an inflammatory disease.

In various embodiments, the IL-17A mediated disease is selected from the group consisting of multiple sclerosis, psoriasis, autoimmune uveitis, asthma and rheumatoid arthritis.

In various embodiments, the IL-17A mediated disease is multiple sclerosis.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings

DETAILED DESCRIPTION

Definitions

Figure 1:
FIG. 1 is a cartoon depicting the non-conventional role of miR4661-3p in mRNA stabilization.
Figure 1:
Figure 2:
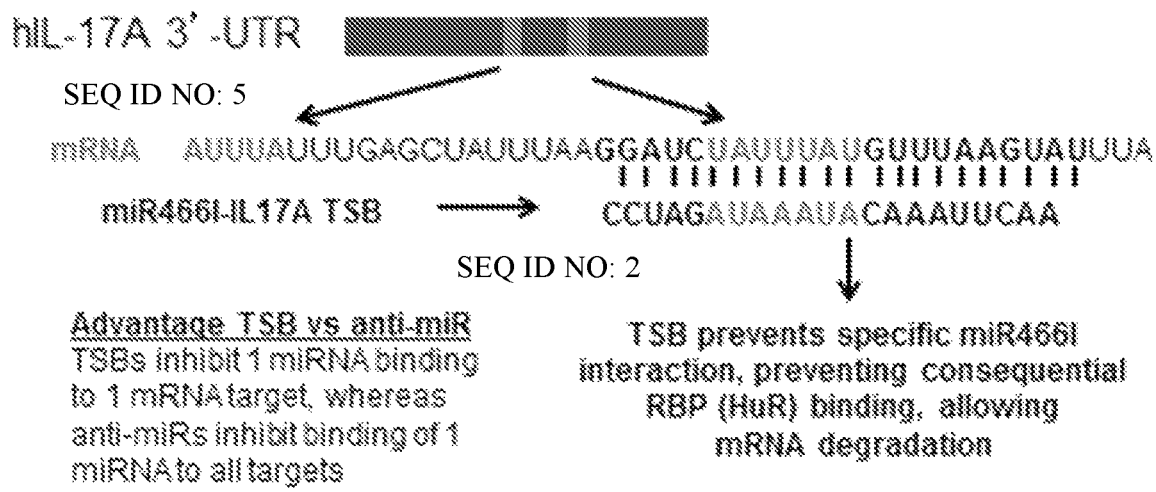
FIG. 2 is a cartoon depicting mir4661-IL17A Target site blockers (TSB).

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, subcutaneous, oral, aerosol, parenteral, ophthalmic, pulmonary and topical administration.

An "effective amount" or "therapeutically effective amount" of a compound is that amount of compound that is sufficient to provide a beneficial effect to the subject to which the compound is administered. An "effective amount" of a delivery vehicle is that amount sufficient to effectively bind or deliver a compound.

As used herein, "IL-17A" may refer to interleukin-17A protein, the IL17A gene (UniProt—Q16552), any mRNA encoded by the gene or any homolog thereof. Human IL17A is encoded by the nucleic acid sequence SEQ ID NO: 1:

AACAGAAAATCTCGTGTCTCTTGAACCTAGTTATTTATTCCTT

GAGCAGAGTAGATATTCAACAAAAGAATTGTTAAATTCAAT

TAAATAGGATATATCTTATTATTAAATATTTTTTCATTTTTT

GTTTACTTATATGATGGGAACTTGAGTAGTTTCCGGAATTGT

CTCCACAACACCTGGCCAAGGAATCTGTGAGGAAAAGAAAG

ATCAAATGGAAAATCAAGGTACATGACACCAGAAGACCTAC

ATGTTACTTCAAACTTTTTCTTCCTCATGAACCATTAAAATA

GAGCATAACTCTTCTGGCAGCTGTACATATGTTCATAAATAC

ATGATATTGACCCATAGCATAGCAGCTCTGCTCAGCTTCTAA

CAAGTAAGAATGAAAAGAGGACATGGTCTTTAGGAACATGA

ATTTCTGCCCTTCCCATTTTCCTTCAGAAGGAGAGATTCTTCT

ATGACCTCATTGGGGCGG

AAATTTTAACCAAAATGGTGTCACCCCTGAACCCACTGCGAC

ACGCCACGTAAGTGACCACAGAAGGAGAAAAGCCCTATAAA

AAGAGAGACGATAGCGCTACATTTTGTCCATCTCATAGCAG

GCACAAACTCATCCATCCCCAGTTGATTGGAAGAAACAACG

ATGACTCCTGGGAAGACCTCATTGGTGGTGAGTCCTGCACTA

ACGTGCGATGCTCTTGCTGATTTGGACCAGATAGTATTTCTG

GACCGTGGGCATGAAACGCTGGGTTCTGACTATGGAGATCC

AGGAATACTGTATATGTAGGATAGGAAATGAAAGCTTTGGT

AGGTATTTAAGTCATTGTGCAGCATTTTCAAGAACTGATACA

CAGCAGTTTGAAAGATAAGATTAAAACTGAAAGATAGCTAT

ATTGGGGCTAAACCACACAAGAAGTGTCACATGATGCTGTG

CAGTAAGAAAGAAAATTTATTGAAAGTCTGTTTTTCTGAGTA

CAAAGGATTTAATATAATTCTCCCACGGCATTTTTCTTTAAA

ATGGGTCACTATCCTTGAGATTTTGAAAGCCGTAGCAGCAAC

AACCTTTGTTTCCATTATCTCGTACCATATTCTCAGTACATTG

AAACTATGTATTCTAACTAAACATAGGTATAACTGTGTTTTA

GAATAAGTGGGGTTTATATTTTTAAATATTTAACTTCAAGT

ATCTTTTTTGAAATCTGATTTTATTACAGAATCAATACATGTT

AAATTTAGAACAACTGGAAAATATACCTAAGAAAACATGAA

GGAGATCGAGTTTTTAGTTGGATGCCTGCCAGTAGCACCAAC

AGCACTTCTAGCATGAATATTGATACCACATAGATTTTCTAT

AGCTCTTTCTTCCAATGTGAATGTTTGACTTCACGATGAGTTT

CACAGAATATGGGACTGAGAACAATGGTGCAGGAGGATATT

TCTACCTAGAAAATCAAGGTTATTATTCCTTCCCAGACCTGA

CAATGATGCATGTGCTGATAGGCTAATGACATGCCATGACTT

GACATTTTTATTAAAATTATTGCCAACCAATGGATAACATGT

CTTTCCTAAGTCAAAAGGAGAATGTTGAAACTAGTTTTTTTA

AAAAAATTTTAAAGCCATGGTGTTAACATTATGTTGGTCATC

TACCTAGATTTTTCTCTAGCTGATCTGAAAAATGTAGTATAG

ATTGTCCTGGAACATTGTGTGTTCTCTATGATTAGCAATGCA

TCATCATCACAATTAATTTGTCAAAAAGAACCACATAGTAAT

CTAATCTCCAACCTCTCTCTCCTTTCCCATTCAATTCTAGTCA

CTGCTACTGCTGCTGAGCCTGGAGGCCATAGTGAAGGCAGG

AATCACAATCCCACGAAATCCAGGATGCCCAAATTCTGAGG

ACAAGAACTTCCCCCGGACTGTGATGGTCAACCTGAACATC

CATAACCGGAATACCAATACCAATCCCAAAAGGTCCTCAGA

TTACTACAACCGATCCACCTCACCTTGGAATCTCCAGTACGT

AAAGCTTCCAGATAAAAATGCTATATTCTTCATCCCTCTTAT

GCATCAGACTGCCAGTTAAATCTCCCTGAGGATGATTTTATT

CATTTAGAATTACCAGTCAAACCTGGAAGGACCACTGTGAA

GAGCAATTCTCAAACTTTCTACAGATTTCTTTAACCAAGCAC

AGGACAGCCTCCAATAATCCCTATCCTGTTAGATCTAATTGT

CACTGACACCAATAATCAACCCAAATTAATTATAATCATTAT

TCTAATATTTATGAGACCCCAAGTCTATTCTTTATTTATTCAA

AGAATAGACATTTATCAAAGAGGATTAATGCTTTTATTATCT

TAACCAGAGCTGCCATTGAGAAGATTTATTGCAAATAATTA

-continued

```
ATAATTAGGGTTTTTTACTTTTATTCTTTTGCTTATTTTTGTTT
TTGAATCCCAGTGGAATAAGTATCACTGGGGTATTTCTACCC
CTTTGTGTGTTAAATAGTCTTGATCTACTTCCTAACATACCTA
TGCTTGCTGTATCCTTAGTATACCCAGTATTTAGACCCCATC
AAGGGTTAAATACCAAATGTATTTTGATCATTTGACTTCATA
CAAATAAGTCTCTGTTCTGTGGAGCCTACAGATTGGTCTGAT
TGTAGGATTTCTTCTCTTCTTCCCATTACTAGGAAGAGTCAA
AATAAATCAATTCAAAAATGCAAGCAAATCATTCACTGATC
TAAAAGAGAGAGGGAAGAGAAGGTCATAGAGACACTTAAC
CTTTTGTTTCCAGCCCTTTATCTCAGCTCTGGGCTCTGTCCCA
CGAATGTGATCTCAGATAAAATTTTGATGTATTCCCTCTTCA
AAGACAGACTTCATCAAGTCAAATAAACAGCTATCTTATTCT
AGATGGTTCCAAGTCTACTCTTCCTTTGGTCTT
CTTCTGTCTGTCAAATGTACCCTAAAAAAGCTATCATTTGTG
TCAAACTTAAATTTTTTCTGTGGCCTCAGTCTATCTTATTTTA
TTCATTCTTCAAATAAATTGGAGAAAAACTGATCACTGTCTT
CTTTTCTATAACAATTCACGTGCTTGAAAAAAAAATCCAATT
TGTCCCCAAAGTTCTTCTTCAAACTAACATCATTTAAAGAAT
TTGCAATGCCTATAATTTGTCATCCTGTGAACTTGCCTCTCTT
CATGTATTCCTGTTTTATTTCTTTCCCACTTTACCAGGAATTC
ACTTTCCTCCTGATTTTTCTCCCCTCTGCAGCCGCAATGAGG
ACCCTGAGAGATATCCCTCTGTGATCTGGGAGGCAAAGTGC
CGCCACTTGGGCTGCATCAACGCTGATGGGAACGTGGACTA
CCACATGAACTCTGTCCCCATCCAGCAAGAGATCCTGGTCCT
GCGCAGGGAGCCTCCACACTGCCCCAACTCCTTCCGGCTGG
AGAAGATACTGGTGTCCGTGGGCTGCACCTGTGTCACCCCG
ATTGTCCACCATGTGGCCTAAGAGCTCTGGGGAGCCCACACT
CCCCAAAGCAGTTAGACTATGGAGAGCCGACCCAGCCCCTC
AGGAACCCTCATCCTTCAAAGACAGCCTCATT
TCGGACTAAACTCATTAGAGTTCTTAAGGCAGTTTGTCCAAT
TAAAGCTTCAGAGGTAACACTTGGCCAAGATATGAGATCTG
AATTACCTTTCCCTCTTTCCAAGAAGGAAGGTTTGACTGAGT
ACCAATTTGCTTCTTGTTTACTTTTTTAAGGGCTTTAAGTTAT
TTATGTATTTAATATGCCCTGAGATAACTTTGGGGTATAAGA
TTCCATTTTAATGAATTACCTACTTTATTTTGTTTGTCTTTTTA
AAGAAGATAAGATTCTGGGCTTGGGAATTTTATTATTTAAAA
GGTAAAACCTGTATTTATTTGAGCTATTTAAGGATCTATTTA
TGTTTAAGTATTTAGAAAAAGGTGAAAAAGCACTATTATCA
GTTCTGCCTAGGTAAATGTAAGATAGAATTAAATGGCAGTG
CAAAATTTCTGAGTCTTTACAACATACGGATATAGTATTTCC
TCCTCTTTGTTTTTAAAAGTTATAACATGGCTGAAAAGAAAG
```

-continued

```
ATTAAACCTACTTTCATATGTATTAATTTAAATTTTGCAATTT
GTTGAGGTTTTACAAGAGATACAGCAAGTCTAACTCTCTGTT
CCATTAAACCCTTATAATAAAATCCTTCTGTAATAATAAAGT
TTCAAAAGAAAATGTTTATTTGTTCTCATTAAATGTATTTA
GCAAACTCAGCTCTTCCCTATTGGGAAGAGTTATGCAAATTC
TCCTATAAGCAAAACAAAGCATGTCTTTGAGTAACAATGAC
CTGGAAATACCCAAAATTCCAAGTTCTCGATTTCACATGCCT
TCAAGACTGAACACCGACTAAGGTTTTCATACTATTAGCCAA
TGCTGTAGACAGAAGCATTTTGATAGGAATAGAGCAAATAA
GATAATGGCCCTGAGGAATGGCATGTCATTATTAAAGATCA
TATGGGGAAAATGAAACCCTCCCCAAAATACAAGAAGTTCT
GGGAGGAGACATTGTCTTCAGACTACAATGTCCAGTTTCTCC
CCTAGACTCAGGCTTCCTTTGGAGATTAAGGCCCCTCAGAGA
TCAACAGACCAACATTTTTCTCTTCCTCAAGCAACACTCCTA
GGGCCTGGCTTCTGTCTGATCAAGGCACCACACAACCCAGA
AAGGAGCTGATGGGGCAGAACGAACTTTAAGTATGAGAAAA
GTTCAGCCCAAGTAAAATAAAAACTCAATCACATTCAATTCC
AGAGTAGTTTCAAGTTTCACATCGTAACCATTTTCGCCCCCA
TGGCCCATGTGCTGTCTTGCCCTACTTCTGAAGGCCTCTAGA
TATTCTCAGGCCACTCTGCAGGCTCCCTGCTTCTTGAAAGAC
CTTCCTCTTCACTCCATCCTGCTCCATCCAGTGTGCTCCAGCC
CACCCAGAGGCCCATGGCTTTTCTAGGCTTCTTTCCCTATTCC
AAATCCAGGGGTTGGCCTCTCCAGCCACCTCCTCTCAGTCAT
TTTGTGCTCACATCTTGATTCCTGTGACCATCCCTGTCACCAT
TTTCCTACAGGAAATCCCCAGGCAGCTTCCAGGGACAGTTCC
TCACAGCCTTTACGCTTTCAAGCTTCTCACTAAAAACCTGCT
GCTCGTTTTCAAGCTTTCTCTGAACGGTGATGATGAAAAGAA
AAAATTGTTTTGTTTTTGTTGGGAGAGGGAGTTGTAAAGGA
TGTATATGTCTATATGTGTGTGTGTGTGTGTGTGGTCCT
GAACCATTATTTCCCACTAGATTTTGGGTGGGGGGTATGCGG
ATGGGAAGAGGCAGTTGCTTTCCATGTACTCCTCCCCTGATA
CACTTTGCTTTTATTCTCTCTTCATTTTCCCCAGTTAGCACTA
CCAT
```

The binding site for miR4661-3p in the mRNA corresponding to the above DNA sequence is underlined.

and/or having the amino acid sequence SEQ ID NO: 3:

```
MTPGKTSLVS LLLLLLSLEAIVKAGITIPRN PGCPNSEDKN
FPRTVMVNLNIHNRNTNTNP KRSSDYYNRS TSPWNLHRNE
DPERYPSVIW EAKCRHLGCINADGNVDYHM NSVPIQQEIL
VLRREPPHCP NSFRLEKILV SVGCTCVTPIVHHVA
```

As used herein, the term "IL-17A-mediated disease" refers to any disease or disorder in which IL-17A contributes, directly or indirectly, to the pathology of the disease or any disease or disorder which may be treated or prevented by altering the expression of IL-17A.

As used herein, the term "locked nucleic acid" refers to a modified RNA nucleotide or polynucleotide with a covalent bond between the 2' oxygen and the 4' carbon of the pentose.

As used herein, the term "bridged nucleic acid" refers to a modified RNA nucleotide or polynucleotide with a bridging structure that limits the degrees of morphological freedom relative to unmodified nucleic acids.

As used herein, the term "phosphorothioate nucleic acid" refers to a modified RNA nucleotide or polynucleotide in which the phosphodiester bond has been replaced with a phosphorothioate bond.

As used herein, the term "peptide nucleic acid" refers to a modified RNA nucleotide or polynucleotide in which natural nucleotide bases are linked to a peptide-like backbone instead of the sugar-phosphate backbone found in DNA and RNA.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, "treating a disease or disorder" means reducing the frequency with which a symptom of the disease or disorder is experienced by a patient. Disease and disorder are used interchangeably herein.

As used herein, the term "treatment" or "treating" encompasses prophylaxis and/or therapy. Accordingly the compositions and methods of the present invention are not limited to therapeutic applications and can be used in prophylactic ones. Therefore "treating" or "treatment" of a state, disorder or condition includes: (i) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition, (ii) inhibiting the state, disorder or condition, i.e., arresting or reducing the development of the disease or at least one clinical or subclinical symptom thereof, or (iii) relieving the disease, i.e. causing regression of the state, disorder or condition or at least one of its clinical or subclinical symptoms.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

Compositions

The invention provides compositions comprising an oligonucleotide complementary to a mir4661-IL17A target site on IL-17A mRNA. Although miRNAs are typically understood to promote the degradation or block translation of their target mRNAs, this relationship is reversed with respect to mir4661-IL17A and IL-17A mRNA such that mir4661-IL17A increases, rather than decreases, the expression of IL-17A (see FIG. 1). Therefore, without wishing to be limited by theory or bound to a particular use, the compositions of the invention are target site blockers (TSB), which bind to a mir4661-IL17A target site on the IL-17A mRNA and prevent the binding of mir4661-IL17A. This blocks the enhancing effect of mir4661-IL17A on the level of expression of IL-17A resulting in a lower level of IL-17A.

In one aspect, the invention provides a composition comprising a polyribonucleic acid comprising (ATAAATA) and at least one modification selected from the group consisting of locked nucleic acid, bridged nucleic acid, phosphorothioate nucleic acid and peptide nucleic acid.

In various embodiments, the polyribonucleic acid may be encoded by a deoxyribonucleic acid comprising the sequence SEQ ID NO: 4 ACTTAAACATAAATAGATCCT. In various embodiments the polyribonucleic acid is a locked nucleic acid with a phosphorothioate backbone.

As discussed in more detail below, the composition may be formulated to facilitate delivery by various routes of administration. In various embodiments, the composition further comprises at least one pharmaceutically acceptable excipient.

Methods of Treating Disease

In another aspect, the invention provides a method of treating an IL-17A mediated disease in a subject in need thereof by providing a therapeutically effective amount of a pharmaceutical composition comprising an oligonucleotide complementary to a mir4661-IL17A target site on IL-17A mRNA. In various embodiments, the IL-17A mediated disease is an inflammatory disease. In various embodiments, the inflammatory disease is selected from the group consisting of multiple sclerosis, psoriasis, autoimmune uveitis and rheumatoid arthritis. As discussed in Example 3, in various embodiments, the composition is administered locally to a target area.

Administration/Dosage/Formulations

The regimen of administration may affect what constitutes an effective amount. The therapeutic formulations may be administered to the subject either prior to or after the onset of the noted inflammatory diseases. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat an inflammatory disease in the patient. An effective amount of the therapeutic compound necessary to achieve a therapeutic effect may vary according to factors such as the state of the disease or disorder in the patient; the age, sex, and weight of the patient; and the ability of the therapeutic compound to treat an inflammatory disease in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of an inflammatory disease in a patient.

The carrier may be a solvent or dispersion medium containing, for example, water, ethanol, polyol (for example, glycerol, propylene glycol, and liquid polyethylene glycol, and the like), suitable mixtures thereof, and vegetable oils.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 350 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of an inflammatory disease in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

The present invention also includes a multi-layer tablet comprising a layer providing for the delayed release of one or more compounds of the invention, and a further layer providing for the immediate release of a medication for treatment of certain diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of an inflammatory disease in the patient being treated. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in practicing the following examples are here described:

Example 1: miR4661-3p/IL-17A TSB in a Progressive EAE Mouse Model (2D2 Transgenic)

Figure 3:
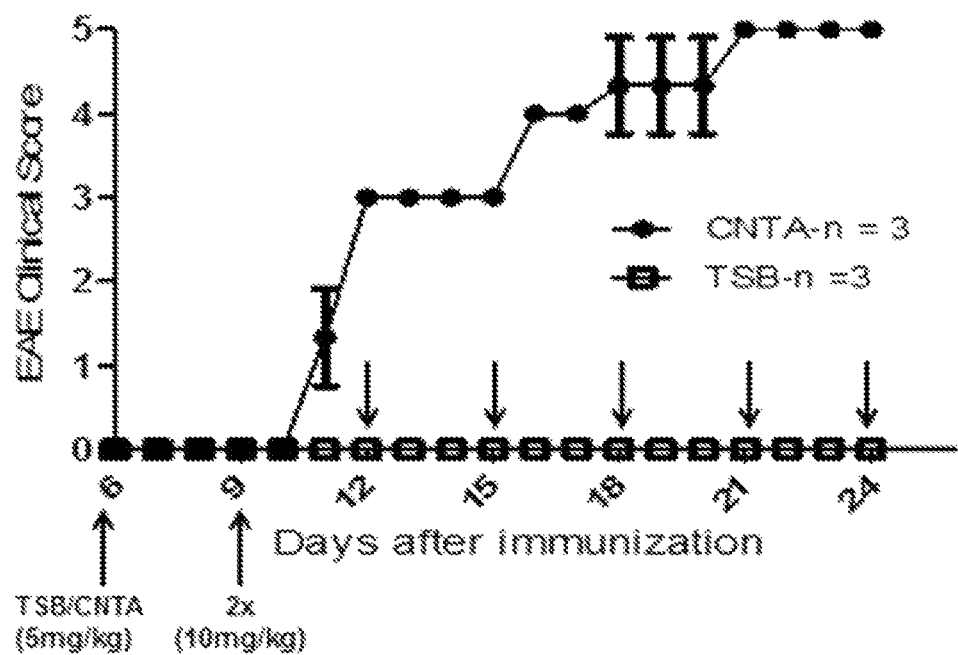
FIG. 3 depicts miR4661-3p/IL-17A TSB in a progressive experimental autoimmune encephalitis (EAE) mouse model (2D2 Transgenic). 2D2-MOG transgenic mice were immunized with an emulsion of zymosan and myelin oligodendrocyte glycoprotein (MOG) peptide on day 0 in 8-10 week old mice, and also treated with pertusis toxin at day 0 and 2. These mice were treated on day 6 with a 5 mg/kg of control oligo (CNTA) or Target Site Blocker (TSB), followed by double dose (10 mg/kg) at day 9 and a single dose every 3 days thereafter. The clinical symptoms were scored on a daily basis until day 40, as follows:
0. Clinically normal
1. Decreased tail tone or limp tail
2. Hindlimb weakness: wobbly gait
3. Hindlimb paralysis and or urinary incontinence
4. Weakness of the hindlimbs and one forelimb
5. Paralysis of all 4 limbs (moribund)
Figure 4:
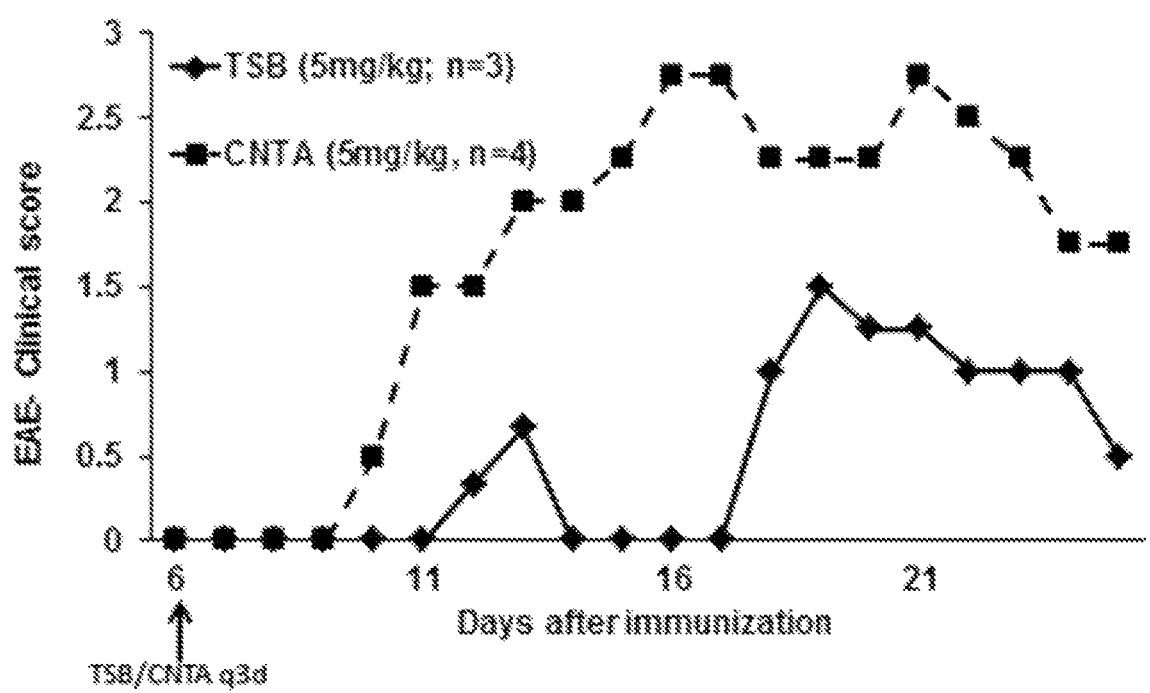
FIG. 4 depicts miR4661-3p/IL-17A TSB in relapsing remitting EAE mouse model. 8-10 week old C57B/6 mice were immunized with an emulsion of zymosan and MOG peptide on day 0 as described above. Starting at day 6, they received 5 mg/kg of CNTA or TSB every 3 days. The clinical symptoms were scored on a daily basis through day 40.
Figure 5:
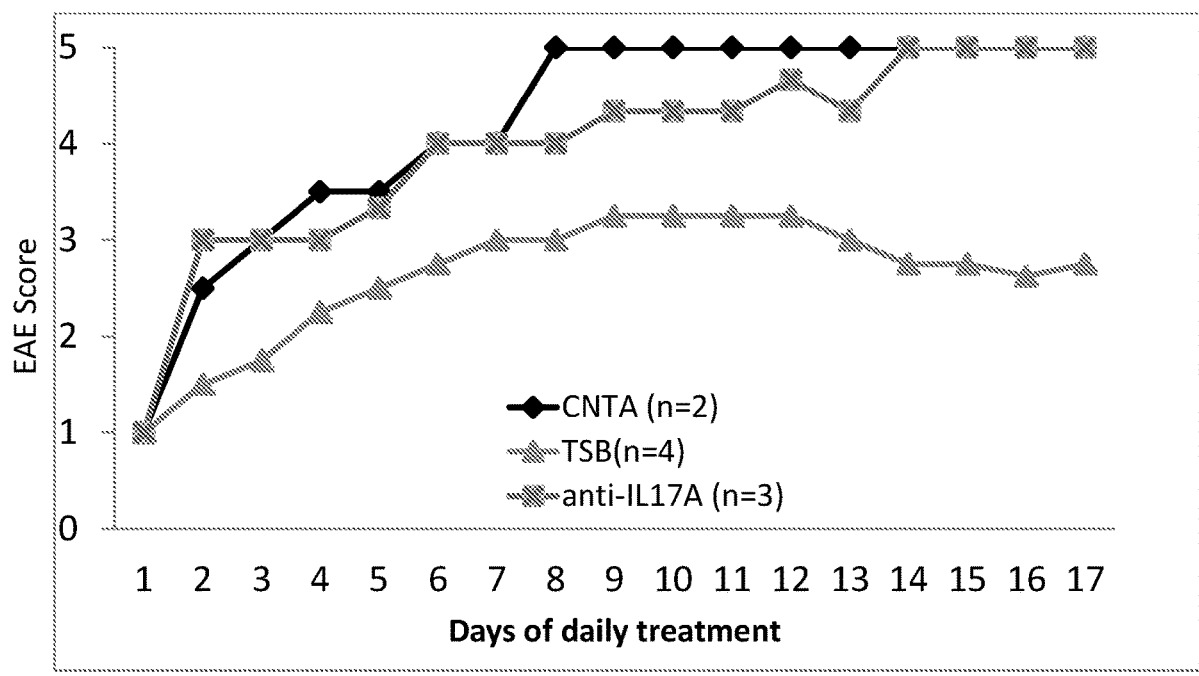
FIG. 5 shows that IL-17A TSB prevents EAE progression in established disease. Mice were given daily intraperitoneal injections with 10 mg/kg TSB, CNTA oligo and 5 mg/kg anti-IL17A antibody (Ab). Disease progresses 4 days after termination of TSB oligo Rx (not shown).

As shown in FIG. 3, 2D2-MOG transgenic mice were immunized with an emulsion of zymosan and MOG peptide on day 0 in 8-10 week old mice, and were treated with pertusis toxin at day 0 and 2. They were treated on day 6 with a 5 mg/kg of control oligo (CNTA) or Target Site Blocker (TSB), followed by a double dose (10 mg/kg) at day 9 and a single dose every 3 days thereafter. The clinical symptoms were scored on a daily basis through day 40, as follows:
  0. Clinically normal
  1. Decreased tail tone or limp tail
  2. Hindlimb weakness: wobbly gait
  3. Hindlimb paralysis and or urinary incontinence
  4. Weakness of the hindlimbs and one forelimb
  5. Paralysis of all 4 limbs (moribund)

Example 2: miR4661-3p/IL-17A TSB in Relapsing Remitting EAE Mouse Model

As shown in FIG. 4, 8-10 week old C57B/6 mice were immunized with an emulsion of zymosan and MOG peptide as described above, followed by 5 mg/kg of CNTA or TSB on day 6 and every 3 days thereafter. The clinical symptoms were scored on a daily basis through day 40 per the scoring criteria above.

Example 3: Treatment with mIL17A TSB Inhibits Psoriasis in Mouse

Figure 6A:
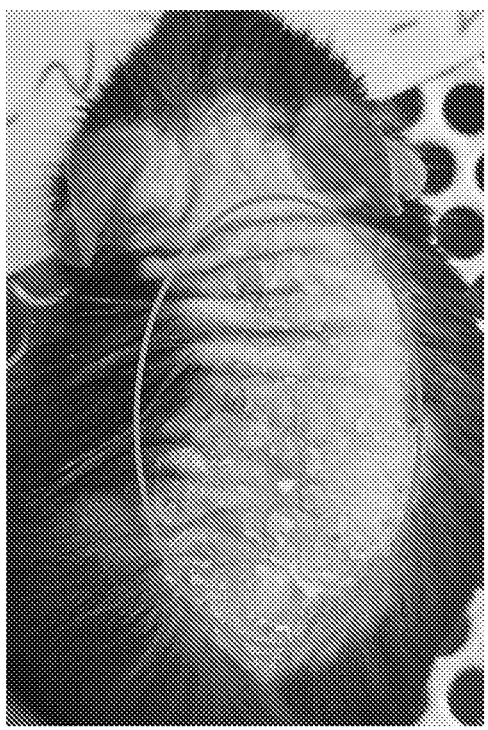
FIG. 6A depicts an imiquimod-induced model of psoriasis with daily topical application of TSB (1 mg/ml) in 10% pluronic vehicle or vehicle alone.
Figure 6A:
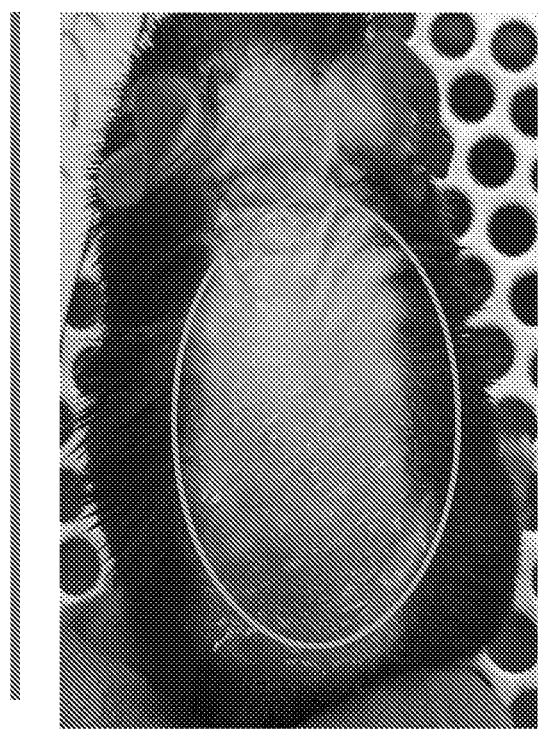

As shown in FIG. 6, C57B/6 mice or IL17A-knockout at the age of 8-9 weeks were shaven. Each mouse was treated topically with 62.5 mg of 5% Imiquimod (Aldara). The treatment with Imiquimod was daily for 5 days. The mIL17A TSB was resuspended in 10% pluronic acid at a concentration of 1 mg/ml for topical treatment. Mice were treated topically with 75 ul of the mIL17A-TSB or vehicle solution over the psoriatic area. The IL17A knockout were not treated with any oligo. Topical treatment with the oligo's occurred 6-7 hours after Imiquimod application.

For intraperitoneal (IP) injections, the mIL17A TSB and a control oligo (CNTA) were resuspended in PBS at a concentration of 1 mg/ml and administered in a volume of 100 ul (at a 5 mg/kg concentration) at the same time with the imiquimod application. Each group of mice consisted of 3 animals. Sera was collected at day 6 in the IP treated mice for IL-17A analysis.

Erythema and scaling was used to score the psoriatic area. The following criteria were used: 0, no signs; 1, slight; 2, moderate; 3, severe; 4 very severe. The cumulative score consists of the erythema and scaling score.

Figure 6B:
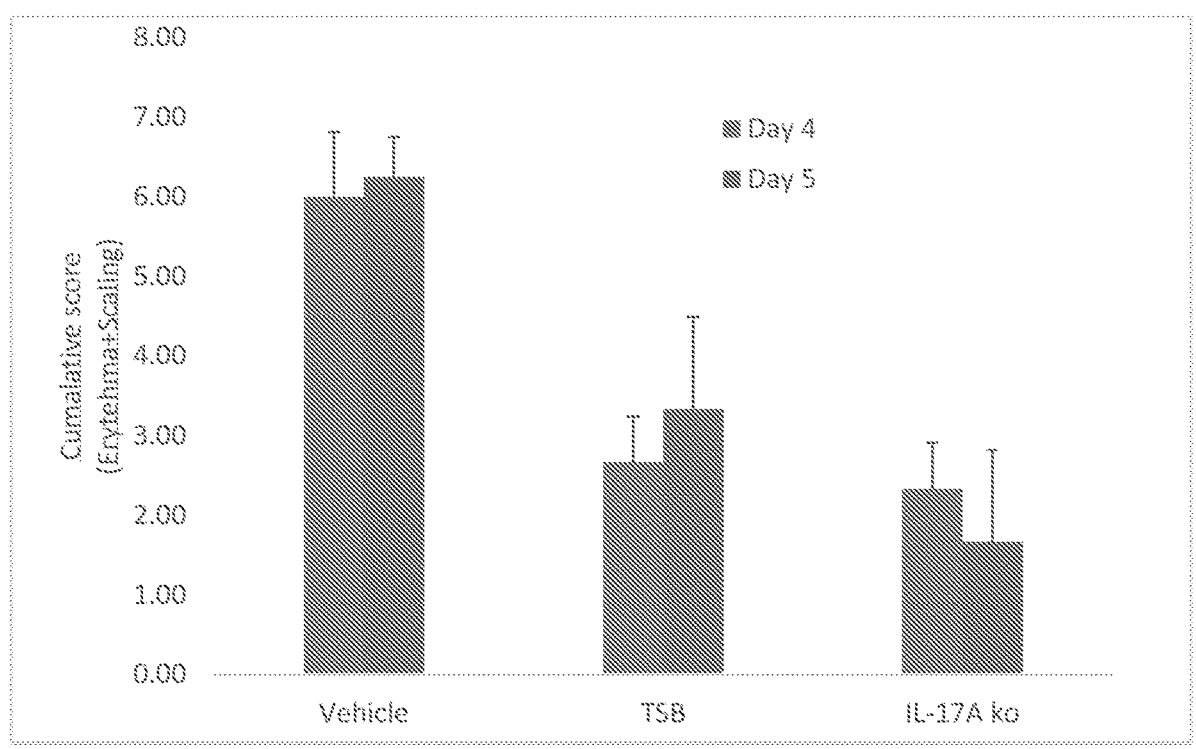
FIG. 6B is a graph depicting Cumulative score (erythema and scaling) of psoriatic mice at most severe phase of disease (day 4 and 5). Daily topical treatment with 1 mg/ml TSB or vehicle, or daily IP 5 mg/ml anti-IL17A Ab. The IL-17A-dependence of the model is demonstrated in IL-17A knockout (ko) mouse
Figure 7:
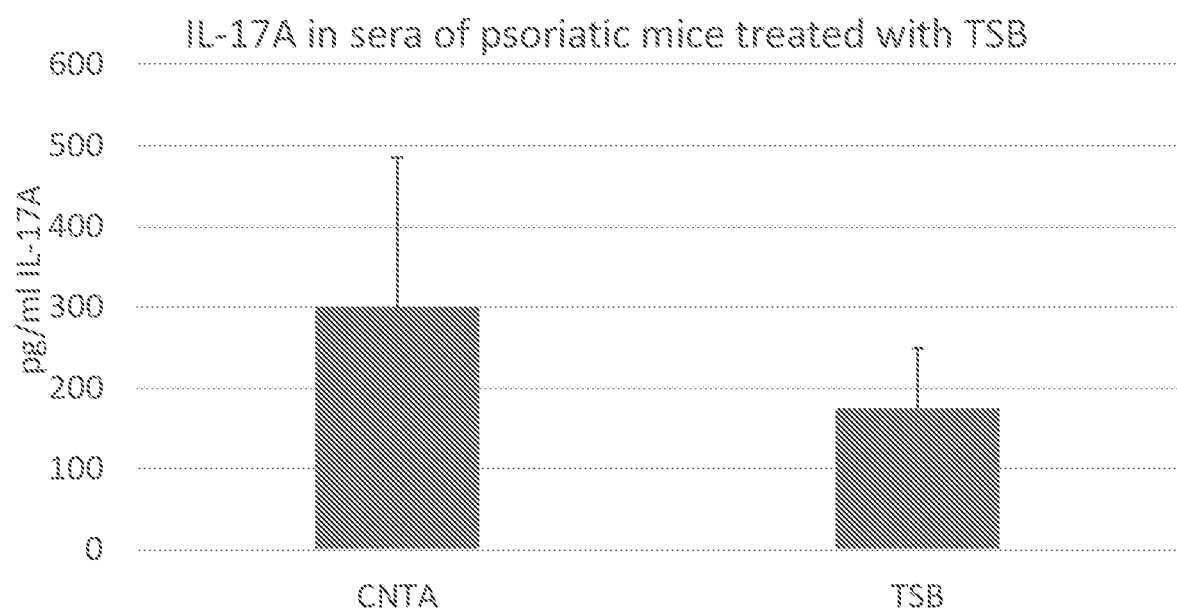
FIG. 7 is a graph depicting IL-17A in sera of psoriatic mice treated with TSB. IL-17A decrease in sera of psoriatic mice injected (IP) daily with 5 mg/kg TSB or CNTA oligo for 6 days.

The mice treated topically with the vehicle (10% pluronic acid in PBS) developed severe erythema and scaling (score of approx. 6), whereas mice treated with the mIL17A TSB had sporadic and mild disease symptoms (score of 3). There was a 50% reduction in the cumulative score. There was slight erythema in mIL17A TSB treated animals which led to a slight increase in the cumulative score. The IL-17A knockout mice which were used as a positive control, hardly developed any visible psoriasis. The disease severity in the mIL17A TSB treated mice was very similar to the disease in IL-17A knockout mice (FIG. 6B). The levels of IL-17A were analyzed in the sera of psoriatic mice that were treated by IP with a CNTA and the mIL17A TSB at 5 mg/kg. In the CNTA mice the IL-17A levels were close to 300 pg/ml and in the mIL17A TSB, these were around 174 pg/ml, a ~42% reduction in IL-17A levels. This strongly implies that topical application of mIL17A TSB psoriasis was effective in down-regulating IL-17A expression and alleviating the disease severity (FIG. 7).

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating an IL-17A mediated disease in a subject in need thereof, comprising administering to the subject a therapeutically effective amount of a composition comprising:
- a polyribonucleic acid encoded by a deoxyribonucleic acid comprising the sequence set forth in SEQ ID NO: 4 (ACTTAAACATAAATAGATCCT),
- wherein the polyribonucleic acid comprises at least one modification selected from the group consisting of locked nucleic acid, bridged nucleic acid, phosphorothioate nucleic acid and peptide nucleic acid.

2. The method according to claim 1, wherein the IL-17A mediated disease is an inflammatory disease.

3. The method according to claim 1, wherein the IL-17A mediated disease is selected from the group consisting of multiple sclerosis, psoriasis, autoimmune uveitis, asthma and rheumatoid arthritis.

4. The method of claim 1, wherein the IL-17A mediated disease is multiple sclerosis.

5. The method of claim 1, wherein the polyribonucleic acid is a locked nucleic acid with a phosphorothioate backbone.

6. The method of claim 1, wherein the composition further comprises at least one pharmaceutically acceptable excipient.

* * * * *